US009863413B1

(12) United States Patent
Wiederin et al.

(10) Patent No.: US 9,863,413 B1
(45) Date of Patent: *Jan. 9, 2018

(54) PERISTALTIC PUMP

(71) Applicant: Elemental Scientific, Inc., Omaha, NE (US)

(72) Inventors: Daniel R. Wiederin, Omaha, NE (US); Gary J. Barret, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/244,544

(22) Filed: Aug. 23, 2016

Related U.S. Application Data

(63) Continuation of application No. 13/184,120, filed on Jul. 15, 2011, now Pat. No. 9,518,576.

(60) Provisional application No. 61/364,474, filed on Jul. 15, 2010.

(51) Int. Cl.
*F04B 43/12* (2006.01)

(52) U.S. Cl.
CPC ...... *F04B 43/1284* (2013.01); *F04B 43/1223* (2013.01); *F04B 43/1253* (2013.01); *F04B 43/1292* (2013.01)

(58) Field of Classification Search
CPC .............. F04B 43/1292; F04B 43/1253; F04B 43/1276; F04B 43/1284; F04B 43/082; A61M 5/14232; A61M 5/1408; A61M 5/1413; A61M 5/1454; A61M 5/50; Y10T 29/4924; Y10T 29/49876; Y10T 403/7073; Y10T 403/7176; Y10T 4/18296; Y10T 74/02
See application file for complete search history.

(56) References Cited

U.S. PATENT DOCUMENTS

| | | | | |
|---|---|---|---|---|
| 3,723,030 A | * | 3/1973 | Gelfand | F04B 43/1292 417/475 |
| 3,832,096 A | * | 8/1974 | Gelfand | F04B 43/1292 417/412 |
| 4,755,109 A | * | 7/1988 | Botts | F04B 43/082 29/453 |
| 4,950,136 A | * | 8/1990 | Haas | F04B 43/1276 417/477.7 |
| 5,257,917 A | * | 11/1993 | Minarik | F04B 43/1292 417/475 |
| 5,266,013 A | * | 11/1993 | Aubert | A61M 5/1413 417/360 |

(Continued)

*Primary Examiner* — Dominick L Plakkoottam
(74) *Attorney, Agent, or Firm* — Advent, LLP

(57) ABSTRACT

A peristaltic pump includes a rotating member operably coupled to a drive. The rotating member includes a plurality of rollers arranged in a circular configuration. A guide member defines a channel configured to direct a peristaltic tube around the rotating member so that the peristaltic tube interfaces with the plurality of rollers. The peristaltic tube is pressed against the plurality of rollers by a retaining shoe. The retaining shoe contains surface irregularities configured to restrict movement of the peristaltic tube. A keeper braces the restraining shoe against the peristaltic tube. The rotating rollers compressing the peristaltic tube against the retaining shoe as the rotating member rotates results in a peristaltic action that produces a nearly pulse free linear flow.

17 Claims, 7 Drawing Sheets

(56) References Cited

U.S. PATENT DOCUMENTS

| | | | | |
|---|---|---|---|---|
| 5,340,290 A | * | 8/1994 | Clemens | F04B 43/1292 417/477.1 |
| 2005/0025647 A1 | * | 2/2005 | Ortega | F04B 43/1253 417/477.1 |
| 2005/0238515 A1 | * | 10/2005 | Kent | F04B 43/1292 417/476 |
| 2007/0104599 A1 | * | 5/2007 | Michels | F04B 43/1253 417/477.1 |
| 2008/0085200 A1 | * | 4/2008 | Michels | F04B 43/1292 417/477.1 |

* cited by examiner

PERISTALTIC PUMP

CROSS-REFERENCE TO RELATED APPLICATIONS

The present application is a continuation under 35 U.S.C. 6120 of U.S. patent application Ser. No. 13/184,120, filed Jul. 15, 2011, and titled "PERISTALTIC PUMP," which itself claims the benefit of 35 U.S.C. §119(e) of U.S. Provisional Application Ser. No. 61/364,474, filed Jul. 15, 2010, and titled "LINEAR FLOW PERISTALTIC PUMP." U.S. patent application Ser. No. 13/184,120 and U.S. Provisional Application Ser. No. 61/364,474 are herein incorporated by reference in their entireties.

BACKGROUND

A peristaltic pump (roller pump) is a type of positive displacement pump used for pumping fluids contained within a flexible tube. A peristaltic pump can use a turning cam to place part of a tube under compression, closing or occluding a section of the tube, and forcing the fluid to be pumped to move through the tube. The tube reopens to its natural state after the passing of the cam. This pumping process may be referred to as peristalsis. Peristaltic pumps may be used in laboratory instrumentation, including sample preparation devices, analytic devices, and so forth. For example, peristaltic pumps may be used to move fluids in a clean or sterile environment without the disturbances resulting from shear forces. Further, it is often desirable to use peristaltic pumps to pump clean, sterile, or aggressive fluids because cross contamination with exposed pump components does not occur.

SUMMARY

A peristaltic pump is disclosed. In one or more implementations, the peristaltic pump includes a rotating member operably coupled to a drive. The drive may be disposed at least partially within a pump housing. The rotating member includes a plurality of rollers coupled to the rotating member in a circular configuration, where the plurality of rollers is configured to orbit about the axis of the rotating member. A guide member coupled to the pump housing defines a channel configured to direct a peristaltic tube around the rotating member so that the peristaltic tube interfaces with the plurality of rollers. The peristaltic tube is pressed against the plurality of rollers by a retaining shoe. The retaining shoe contains surface irregularities configured to restrict movement of the peristaltic tube. The peristaltic pump also includes a keeper for bracing the retaining shoe against the peristaltic tube. The rotating rollers compressing the peristaltic tube against the retaining shoe as the rotating member rotates results in a peristaltic action that produces a nearly pulse free linear flow.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Figure 1:
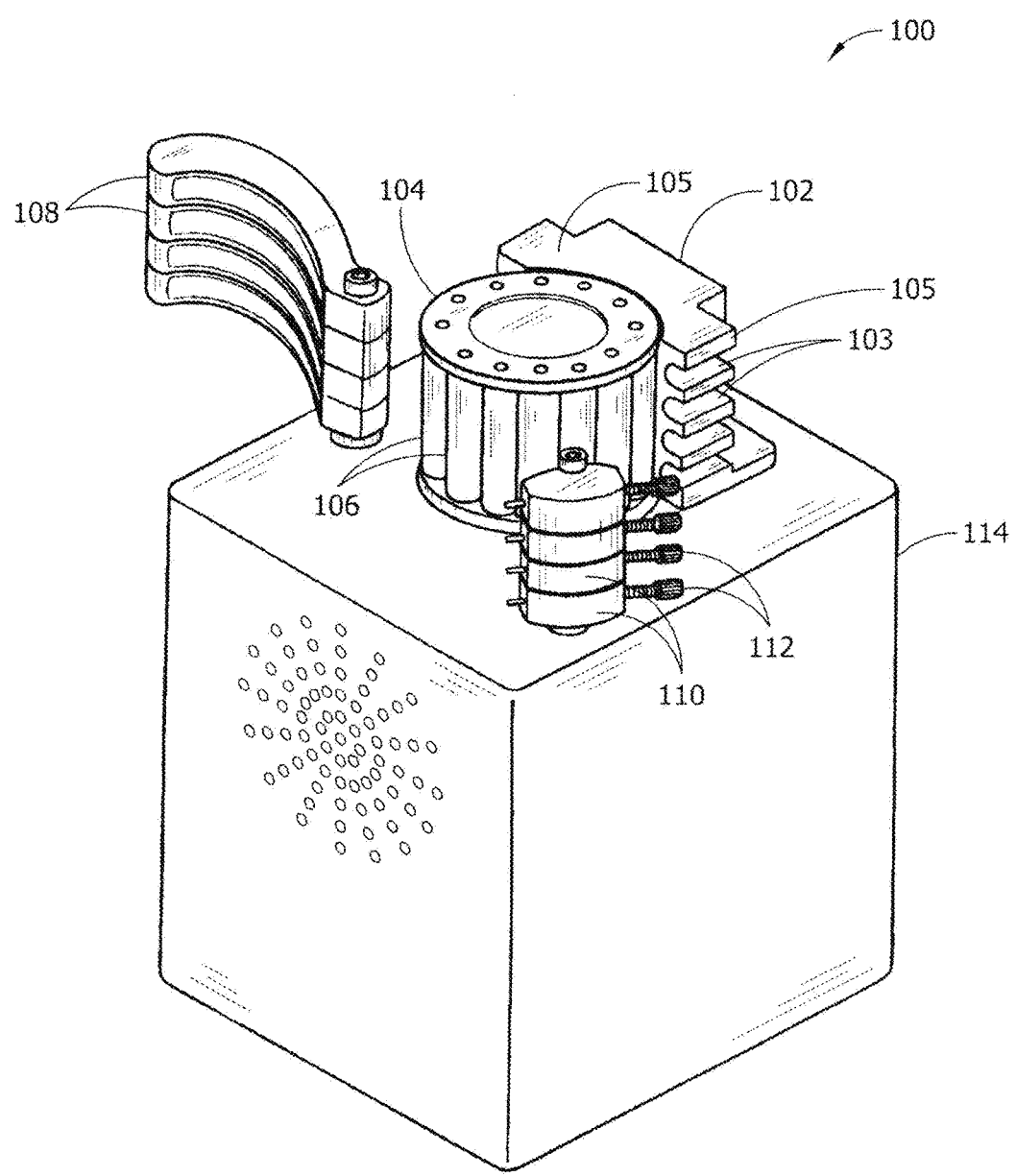
FIG. 1 is an isometric view illustrating a peristaltic pump, shown in an opened position ready to receive a peristaltic tube in accordance with an example implementation of the present disclosure.
Figure 2:
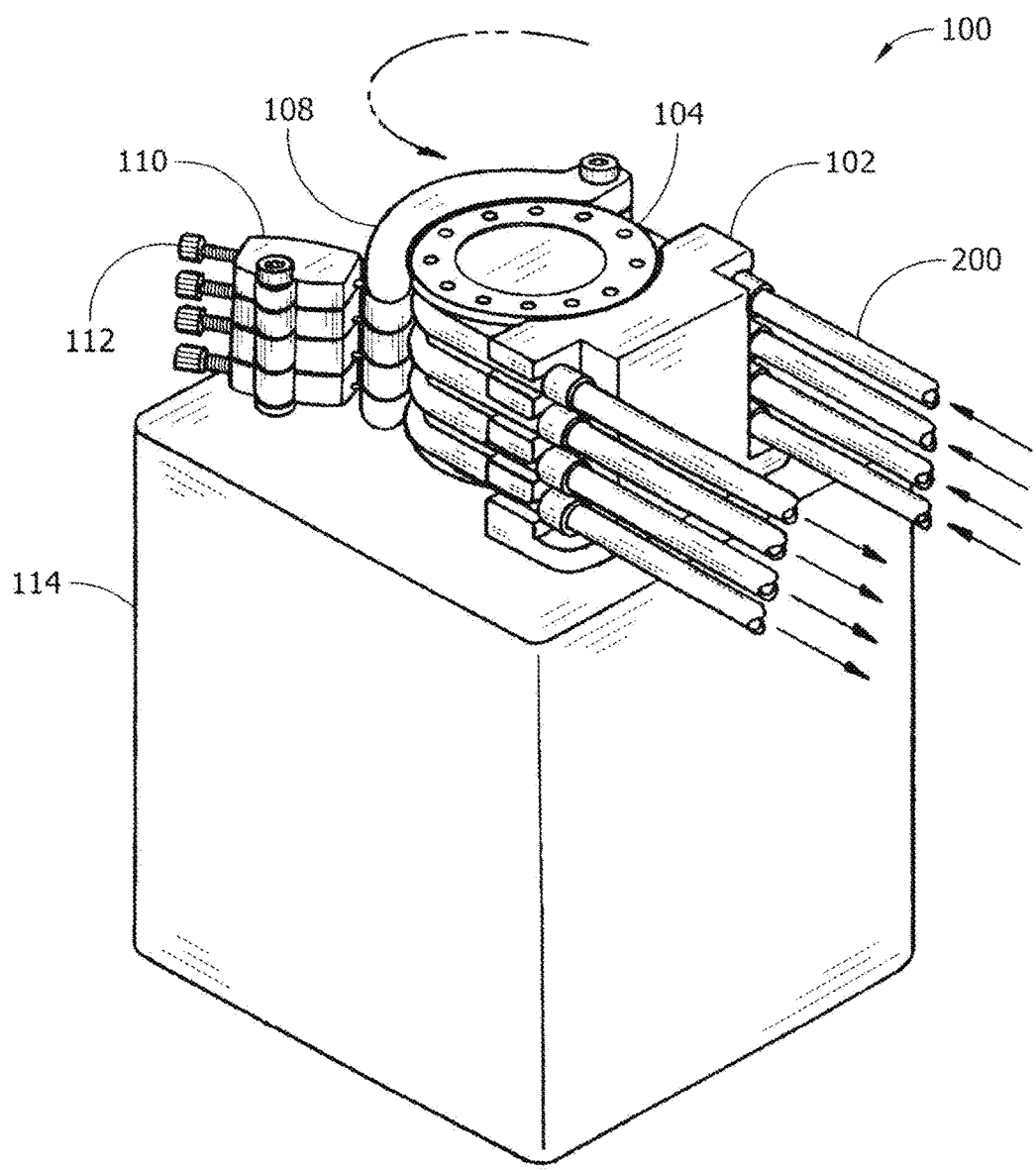
FIG. 2 is an isometric view of the peristaltic pump illustrated in FIG. 1, where the peristaltic pump is shown with peristaltic tubes in a pumping position.

Linear flow is highly desirable in a variety of circumstances. Pulse free or nearly pulse free pumping is also highly desirable. For example, it may be desirable to pump slurries (e.g., suspensions of one or more solids in a liquid), viscous, shear-sensitive, and/or aggressive fluids without subjecting such materials to excessive turbulent mixing, pulsations, and/or shear forces. Accordingly, the present disclosure is directed to a peristaltic pump that can provide both linear flow and nearly pulse free operation. One or more peristaltic tubes are guided through a guide member, around a rotating member with rollers, and back through the guide member. Retaining shoes, braced by a keeper, compress the peristaltic tubes against the rollers. The retaining shoes may include surface irregularities to restrict movement of a peristaltic tube. The rotating member rotates, rolling the rollers along the peristaltic tube. The compression of the peristaltic tube by the rollers results in a peristaltic action that pumps the fluid through the peristaltic tube. The shoe may be configured to compress the peristaltic tube in such a way that only one roller pinches the peristaltic tube at a time. Further, multiple rollers may pinch the peristaltic tube at a time. Implementations of the present disclosure may provide nearly pulse free pumping even at low flow rates. Further, flow rate may be linearly related to the speed of the rotating member, resulting in linear flow.

In the following discussion, example implementations of peristaltic pumps are first described.

Example Implementations

FIGS. 1 through 6 illustrate peristaltic pumps in accordance with example implementations of the present disclosure. As shown, a peristaltic pump may be implemented as a linear flow peristaltic pump 100. The linear flow peristaltic pump 100 may include a guide member 102 for guiding a peristaltic tube 200 around a rotating member 104. The rotating member 104 may be coupled with a number of rollers 106 for contacting the peristaltic tube 200, where the rollers are arranged in a circular configuration generally centered on the axis of rotation of the rotating member 104. Linear flow peristaltic pump 100 may further include a retaining shoe 108 for bracing (pressing) the peristaltic tube 200 against the rollers 106, and a keeper 110 for locking (bracing) the retaining shoe 108 against the peristaltic tube 200. The rollers 106 compressing the peristaltic tube 200 against the retaining shoe 108 provide for a peristaltic pumping action when the rotating member 104 is rotated, causing the rollers 106 to revolve/orbit about the axis of rotation of the rotating member 104. The linear flow peristaltic pump 100 may further include a pump housing 114 for supporting the guide member 102, rotating member 104, retaining shoe 108, and/or the keeper 110. In implementations, the keeper 110 may be adjustable (e.g., movable with respect to the pump housing 114). In other implementations, the keeper 110 may be stationary (e.g., fixed with respect to the pump housing 114). In implementations, the keeper 110 can be integrally formed with the pump housing 114.

Figure 4:
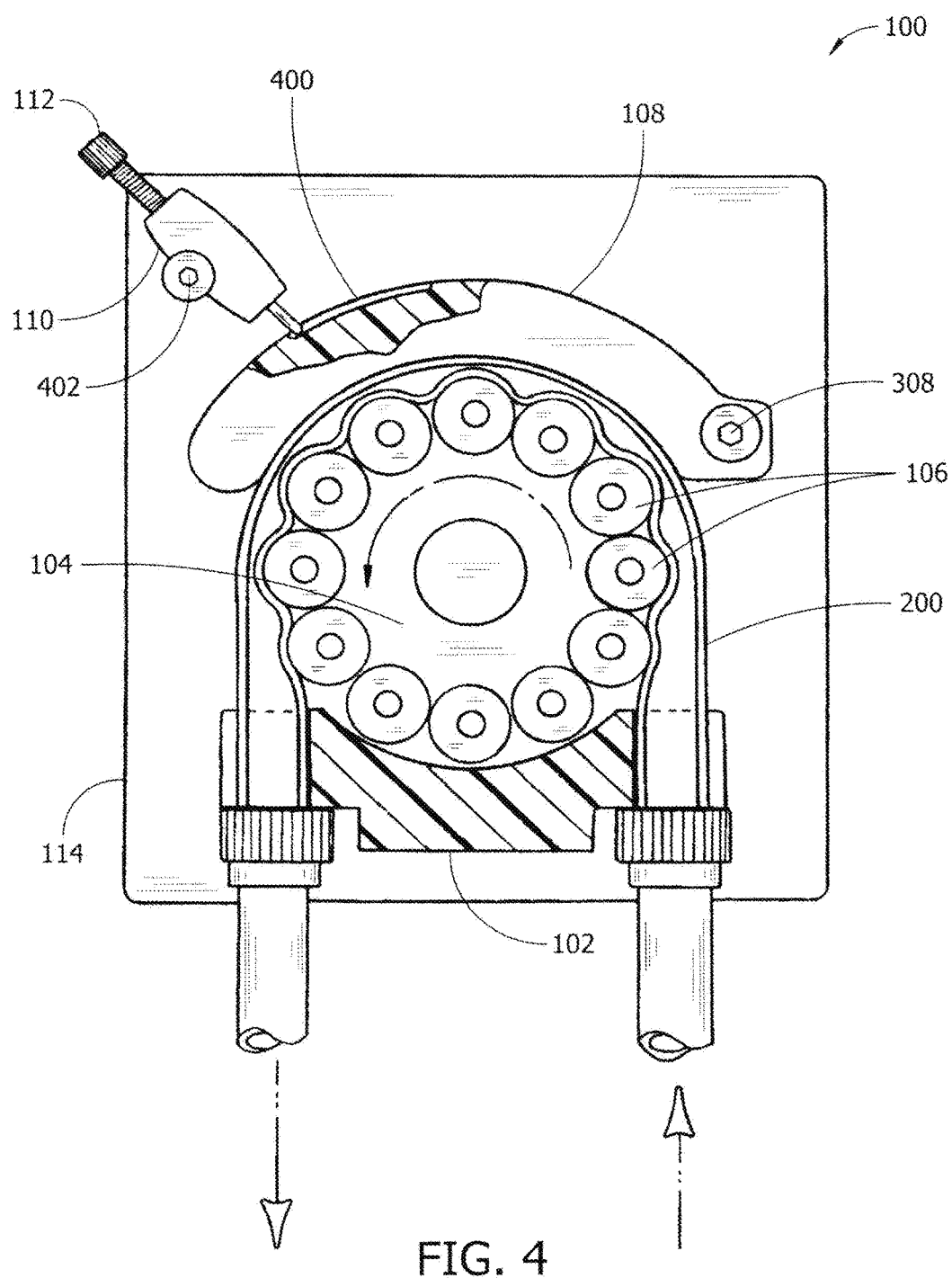
FIG. 4 is a partial cross-sectional top plan view of the peristaltic pump illustrated in FIG. 1, where the peristaltic pump is shown in a pumping position.

Guide member 102 may define a single channel or multiple channels 103. Channels 103 may be configured to guide a tube (e.g., peristaltic tube 200) around the rotating member 104. Guide member 102 may include two guides 105 for a single channel 103 or multiple guides 105 for multiple channels 103. In implementations, guide member 102 can define four channels 103 with two guides 105 for each channel. Further, the guides 105 for each channel 103 can be located on opposing sides of the guide member 102. Thus, it should be noted that channels 103 are not necessarily continuous around the rotating member 104. Peristaltic tube 200 is placed in a semi-elliptical shape as it is guided through the guide member 102 on one side, around the rotating member 104 and guided back through the guide member 102 on the opposite side. Multiple guide members 102 may also be used. Guide member 102 may comprise a concave shape configured to allow the guide member 102 to extend on either side of the rotating member 104 partially around the rotating member 104 (e.g., as illustrated in FIG. 4). Guide member 102 may be formed from a variety of materials including metal, plastic, wood, nylon, ceramic, and so forth. However these materials are provided by way of example only, and are not meant to be restrictive of the present disclosure. In embodiments, guide member 102 may be an integral part of pump housing 114 or may be coupled to pump housing 114.

Figure 5:
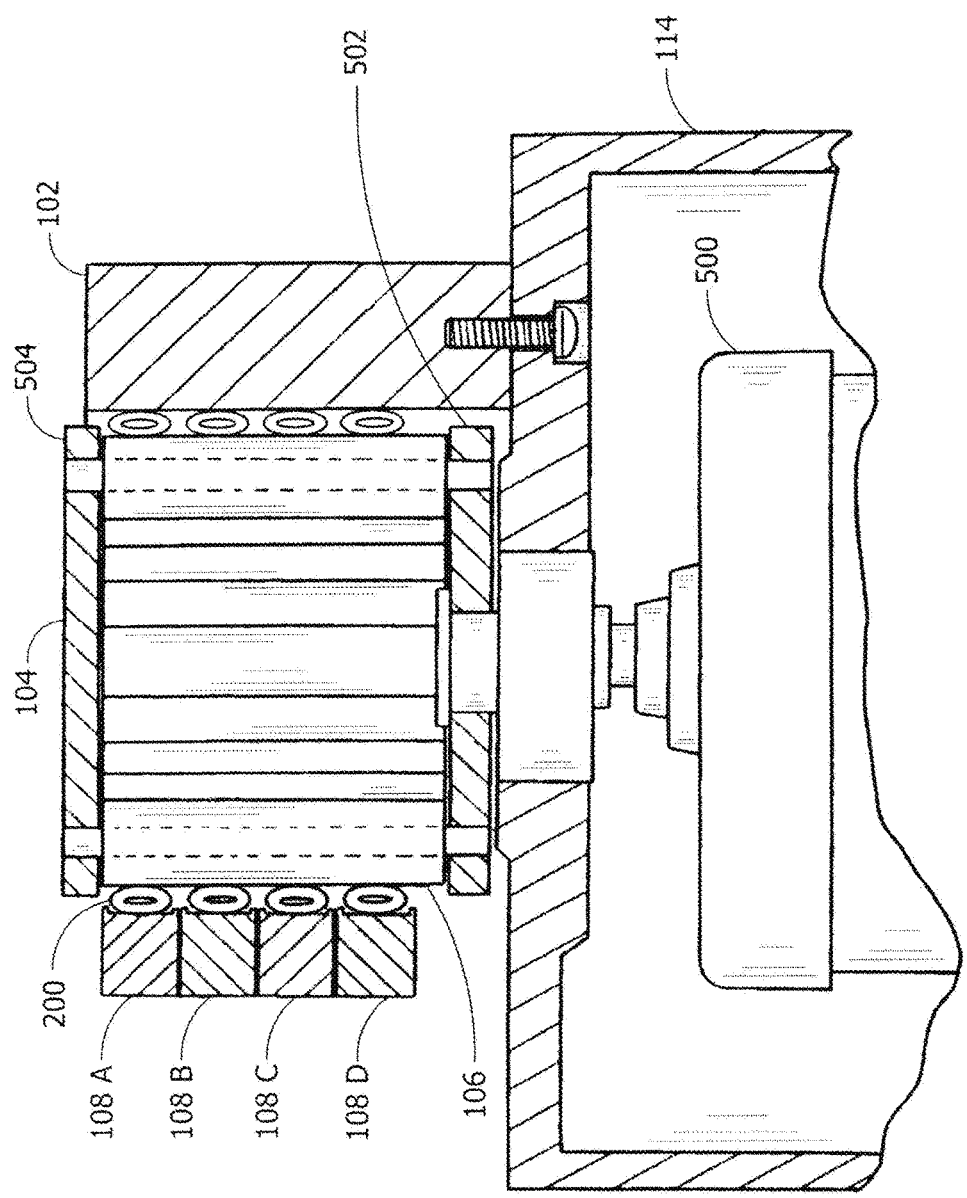
FIG. 5 is a partial cross-sectional side elevation view of the linear flow peristaltic pump illustrated in FIG. 1, where the peristaltic pump is shown in a pumping position.

Rotating member 104 may be substantially cylindrical in nature, having a substantially circular base plate 502 coupled to a substantially circular top plate 504. The base plate 502 and top plate 504 may have the same diameter or different diameters. Base plate 502 and top plate 504 may be configured for supporting rollers 106 in a circular configuration generally centered on the axis of rotation of the rotating member 104. The rollers 106 may be oriented longitudinally perpendicular to the base plate 502 and top plate 504, wherein the length of the rollers 106 may determine the distance between the base plate 502 and top plate 504. Rotating member 104 may be coupled to the pump housing 114 using a bearing, or another rotational support structure. The bearing may provide an axis of rotation for the rotating member 104. Rotating member 104 may further include a receiving end for receiving rotational power from a drive (power source), such as a motor 500, a drive shaft, gearing, and so forth. Rotating member 104 may be operably coupled to the drive. In some implementations (e.g., as illustrated in FIG. 5), rotating member 104 is directly connected to motor 500. In other implementations, rotating member 104 can be coupled to motor 500 via gears or other mechanisms for transferring power from the motor 500 to the rotating member 104. For example, gears may be used to change rotational speed and/or torque characteristics of the power delivered from the motor 500. In implementations, motor 500 can be at least partially contained within the pump housing 114.

In operation, the rollers 106 may compress the peristaltic tube 200 as the rotating member 104 rotates, providing a peristaltic action. Each roller 106 may have a substantially cylindrical shape with a longitudinal axis extending between the base plate 502 and top plate 504 of the rotating member 104. The longitudinal axis of each roller 106 may be substantially parallel to the axis of rotation of the rotating member 104. Rollers 106 may be in a circular configuration around the rotating member 104. Thus, as the rotating member 104 is rotated, the rollers 106 orbit about the axis of rotation of the rotating member 104.

It should be noted that the diameter of a roller 106 with respect to the peristaltic tubing 200 may alter pumping performance. For example, a roller 106 having a smaller diameter may compress a smaller area of peristaltic tube 200 as compared with a roller 106 having a larger diameter. In some implementations, a reduced area of compression may lead to reduced stretching of peristaltic tube 200, leading to improved tube performance and/or a longer usable life for a tube. Further, it should be noted that smaller diameter rollers 106 may allow for an increased number of rollers 106 on rotating member 104 as compared with rollers 106 having a larger diameter. Smaller diameter rollers 106 may alter the increments of fluid pumped. For example, different combinations of roller diameters and numbers of rollers may allow for varying pulsation of fluid pumping. In one specific implementation, twelve (12) rollers 106 may be included with the linear flow peristaltic pump 100. However, in other implementations, more than twelve rollers or fewer than twelve rollers can be included with the linear flow peristaltic pump 100.

Retaining shoe 108 may press the peristaltic tube 200 against the rollers 106. Shoe 108 may include a curvature correlating with the circular configuration of the rollers 106. Further, shoe 108 may include a lower planar surface 301 and a corresponding upper planar surface 303, an inner concave surface 305 correlating with the circular configuration of the rollers 106, and an outer surface 307, which may be convex, planar, concave, or of some other geometry. Shoe 108 may be plastic, metal, wood, nylon and so forth. However these materials are provided by way of example only, and are not meant to be restrictive of the present disclosure.

Shoe 108 may rotate about an axis of rotation 308. Rotation about axis 308 may allow the shoe 108 to compress the peristaltic tube 200 when shoe 108 is in a closed position, and release compression when shoe 108 is in an open position. Peristaltic tube 200 may be accessible when shoe 108 is in an open position. In implementations, axis 308 may be on a single end of the shoe 108 resulting in a pivoting end near the axis 308 and a swinging end opposite the pivoting end.

Figure 3:
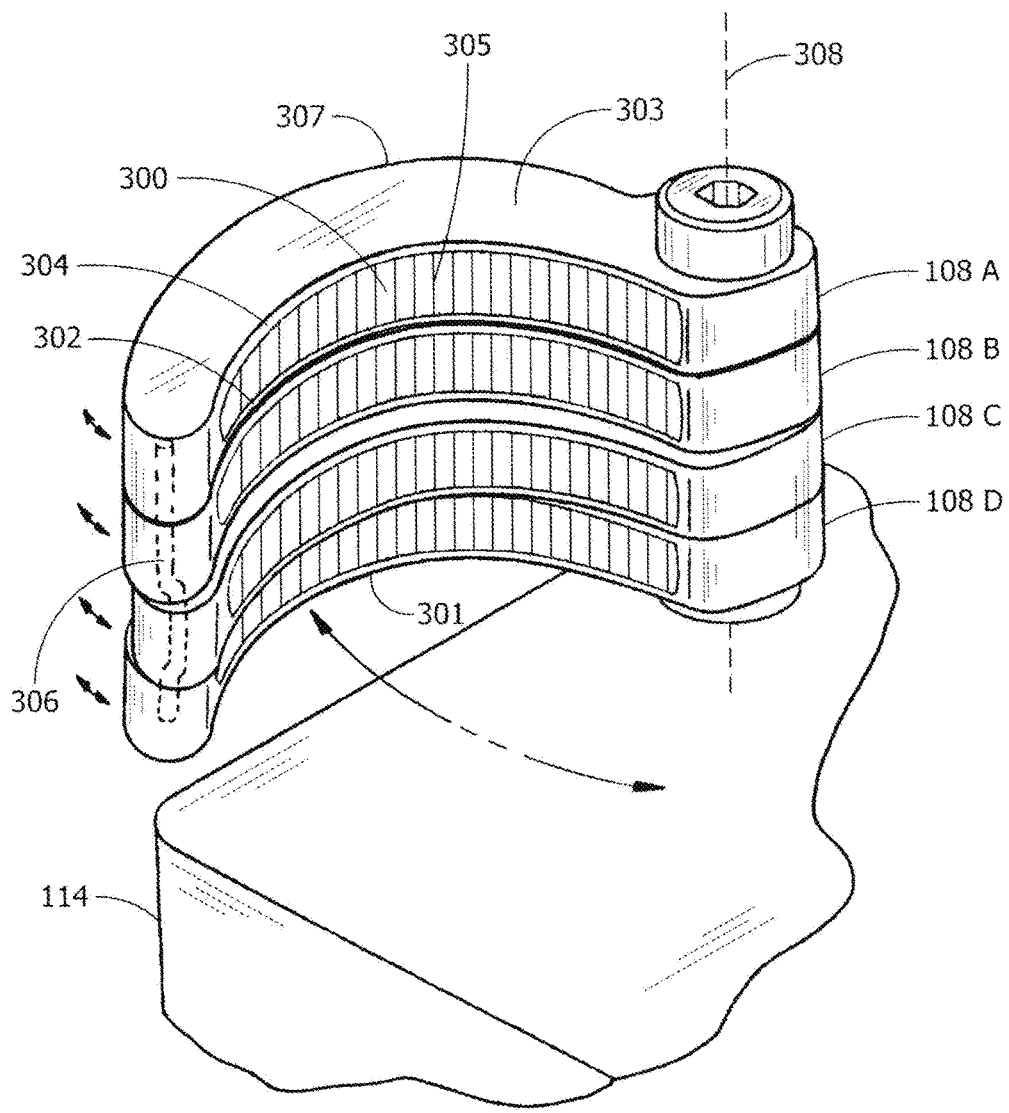
FIG. 3 is a partial isometric view of the peristaltic pump illustrated in FIG. 1, further illustrating retaining shoes in an opened position.

Referring now to FIG. 3, the lower planar surface 301 may extend beyond the inner concave surface 305 resulting in a lower ridge 302. The upper planar surface 303 may also extend beyond the inner concave surface 305 resulting in an upper ridge 304. Lower ridge 302 and/or upper ridge 304 may restrict or prevent the peristaltic tube 200 from moving beyond lower ridge 302 and/or upper ridge 304. FIG. 3 depicts an implementation with four shoes 108 coupled together. Generally, one shoe 108 can be used per channel 103; thus, in a four channel implementation, four shoes 108A through 108D can be used, with one shoe 108 per channel 103. In an implementation with more than one shoe 108 (e.g., as illustrated in FIG. 3), a rod 306 inserted in the swinging end of a number of shoes 108 may be used to keep the shoes 108 together. Rod 306 may be formed of carbon fiber or another material for keeping the shoes 108 together. Each shoe 108 may contain a through hole or a partial hole in the swinging end of the shoe 108, for the purpose of receiving rod 306. In FIG. 3, shoes 108A and 108D include partial holes and shoes 108B and 108C include through holes. The diameter of a through hole or a partial hole may be larger than the diameter of the rod 306, allowing for individual adjustment of each shoe 108, one relative to another. Further, rod 306 may be generally linear, or may include a shape that varies for biasing one or more of the shoes 108 relative to the other shoes, such as the rod 306 seen in FIG. 3, which biases shoe 108C relative to shoes 108A, 108B and 108D. For example, rod 306 may include various segments that are not coaxial with respect to a long dimension of the rod. In FIG. 3, for instance, a longitudinal axis of a segment of rod 306 that extends through shoe 108C is not coaxial with longitudinal axes of rod segments that extend through shoes 108A, 108B, and 108D.

Referring again to FIG. 3, the inner concave surface 305 may contain surface irregularities, such as striations 300. Surface irregularities can include one or more ridges, grooves, marks, and/or disturbances on the inner concave surface 305 that can be raised and/or recessed. In implementations, surface irregularities may occur naturally in a material (e.g. as part of a materials naturally occurring structure) or can be the result of manufacture or process (e.g. machined, molded, and so forth). For example, striations 300 may restrict movement of the peristaltic tube 200 (e.g., restricting lengthwise stretching of the peristaltic tube 200, restricting movement of the peristaltic tube 200 in a longitudinal direction along the lengthwise curvature of the peristaltic tube 200, and/or restricting movement of the peristaltic tube 200 in a lateral direction perpendicular to the lengthwise curvature of the peristaltic tube 200). Further, striations 300 may allow for incremental peristaltic tube 200 segments to be stretched one at a time allowing for low pulse pumping and/or extended tube life.

Keeper 110 may brace the retaining shoe 108 against the peristaltic tube 200. Keeper 110 may rotate about an axis 402. Referring to FIG. 4, shoe 108 may include a receiver 400 to receive the keeper 110. The keeper 110 may function to lock the retaining shoe 108 in place. For example, keeper 110 may rotate about axis 402 and interface with receiver 400 to lock shoe 108 in place. Receiver 400 may be a slot, groove, or another feature for receiving the keeper 110. Keeper 110 may include an adjustment mechanism 112 for adjusting the compression between the shoe 108 and the rollers 106. In implementations, the adjustment mechanism 112 may be a set screw. It should be noted that adjustment of the shoe 108 by adjustment mechanism 112 may have a limited effect on flow rate through a peristaltic tube 200, which may be desirable, such as during extended use of the pump 100 during which different users may operate the pump 100 and use the keeper 110.

Peristaltic tubing 200 may be compressed between the rollers 106 and the shoe 108 to allow fluid to be pumped by a peristaltic action as the rotating member 104 rotates. Referring now to FIG. 5, the compression of the peristaltic tube 200 between the shoes 108 and rollers 106 is shown. Generally, the compression of rollers against a peristaltic tube may function to wear out the peristaltic tube, resulting in limited tube life and memory effects in the peristaltic tube. In implementations of the present disclosure, roller 106 wear on peristaltic tube 200 may be reduced, resulting in improved tube lifetime and reduced memory effects of tube compression.

Figure 6:
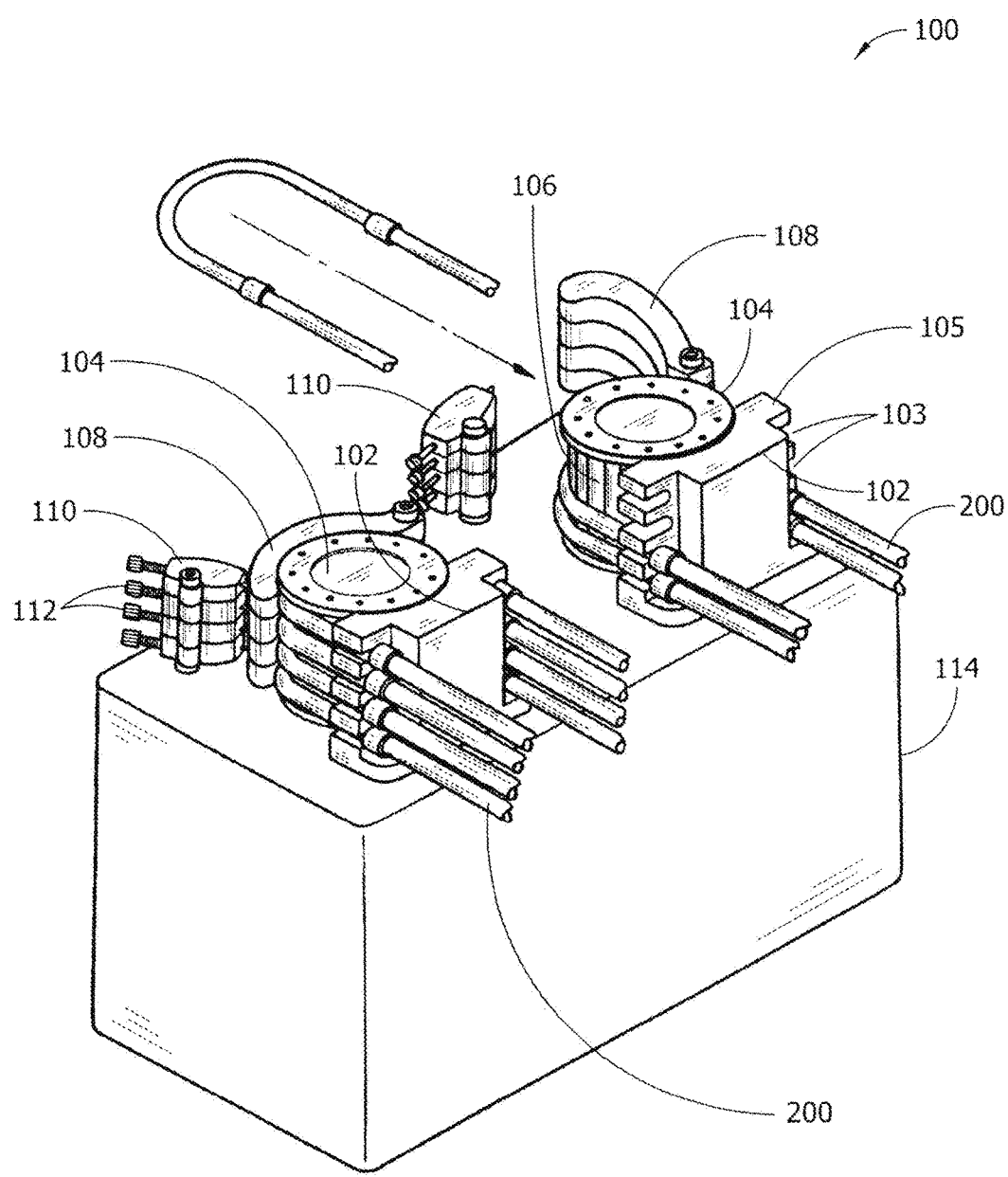
FIG. 6 is an isometric view illustrating another peristaltic pump in accordance with an example implementation of the present disclosure.

Referring specifically to FIG. 6, another specific implementation is shown. A configuration of two linear flow peristaltic pumps 100 is shown. Pumps 100 may be distinct and separate, or may be integrated together in a variety of configurations. Integration may include utilizing a single pump housing 114 as in FIG. 6. Because flow rate is linear, a configuration of more than one linear flow peristaltic pump 100 may be used to mix multiple flow rates. Because the flow rates are linear, desired concentrations or dilutions may be achieved accurately and continuously without a residence chamber. For example, one rotating member 104 of a first peristaltic pump may have a different diameter and/or may be operated at a different speed than another rotating member 104 of another peristaltic pump. Thus, the two pumps may pump at different flow rates. When outputs of the peristaltic pumps are combined, the varying flow rates may provide a resulting mixture that contains a higher concentration of fluid from one pump than from another. By varying the flow rate, this concentration can be changed accordingly. However, two pumps are mentioned by way of example only, and are not meant to be restrictive of the present disclosure. Thus, the outputs of more than two pumps can be combined, such as combining the output of three or more pumps to control mixtures of three or more fluids.

Figure 7:
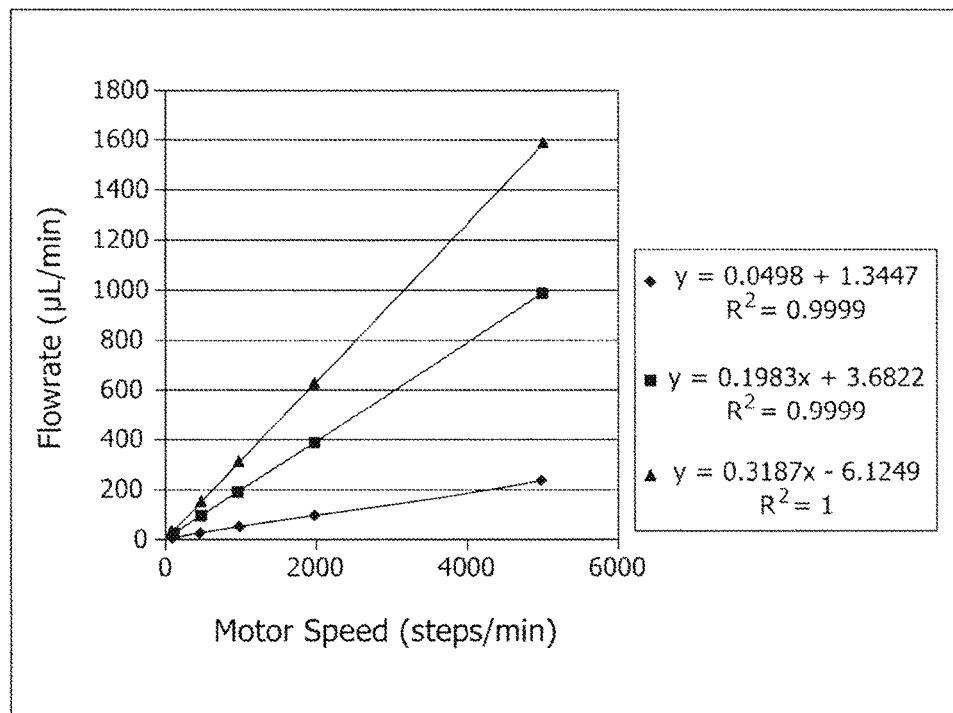
FIG. 7 is a graph illustrating the effect of drive speed on flow rate for a peristaltic pump implemented in accordance with an example implementation of the present disclosure.

Referring to FIG. 7, the effect of drive speed on flow rate is shown for several example implementations. In FIG. 7, flow rate is plotted with respect to drive motor speed through three different peristaltic tubes implemented with peristaltic pumps in accordance with the present disclosure. As shown in FIG. 7, the relationship between flow rate and drive motor speed is at least substantially linear for the three tubes. This can be seen, for example, by $R^2$ measurements corresponding to linear regression analysis of the drive speed vs. flow rate data included in the legend of the graph in FIG. 7. It is noted that the linear relationship may hold for very low flow rates (e.g., as represented by data at or between zero (0) and one thousand (1,000) steps per minute (steps/min) on the graph in FIG. 7).

With reference to other example implementations of the present disclosure, a table containing flow rate calibration for peristaltic pump tubing having various diameters is included below.

| Inside Diameter | Calibration Slope mL/min per RPM |
|---|---|
| 0.13 mm | 0.00060 |
| 0.19 mm | 0.00129 |
| 0.27 mm | 0.00266 |
| 0.38 mm | 0.00468 |
| 0.44 mm | 0.00763 |
| 0.51 mm | 0.00948 |
| 0.57 mm | 0.01144 |
| 0.64 mm | 0.01395 |
| 0.76 mm | 0.01871 |
| 0.89 mm | 0.02423 |
| 0.95 mm | 0.02809 |
| 1.02 mm | 0.03052 |
| 1.09 mm | 0.03320 |
| 1.14 mm | 0.03538 |
| 1.22 mm | 0.04608 |
| 1.30 mm | 0.04714 |
| 1.42 mm | 0.05034 |

-continued

| Inside Diameter | Calibration Slope mL/min per RPM |
|---|---|
| 1.52 mm | 0.05125 |
| 1.65 mm | 0.05500 |
| 1.75 mm | 0.05776 |
| 1.85 mm | 0.06116 |
| 2.06 mm | 0.06356 |
| 2.20 mm | 0.06480 |
| 2.54 mm | 0.06680 |
| 2.79 mm | 0.06860 |
| 3.17 mm | 0.06964 |

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A peristaltic pump, comprising:
a rotating member configured to rotate about an axis;
a plurality of rollers coupled to the rotating member in a circular configuration, the plurality of rollers configured to orbit about the axis of the rotating member;
a guide member coupled to the pump housing, the guide member defining a channel configured to guide a peristaltic tube around the rotating member so that the peristaltic tube is in proximity to the plurality of rollers;
a retaining shoe pivotally coupled to the pump housing, the retaining shoe configured to press the peristaltic tube against the plurality of rollers, the retaining shoe comprising a plurality of surface irregularities, the plurality of surface irregularities configured to restrict movement of the peristaltic tube; and
a keeper coupled to the pump housing, the keeper configured to brace the retaining shoe against the peristaltic tube, wherein the keeper comprises an adjustment mechanism configured to brace the retaining shoe against the peristaltic tube by exerting a force on the retaining shoe opposite a pivot of the retaining shoe and in a direction generally toward the axis of the rotating member.

2. The peristaltic pump as recited in claim 1, wherein the rotating member comprises a top plate and a bottom plate for supporting the plurality of rollers.

3. The peristaltic pump as recited in claim 1, wherein the retaining shoe comprises an upper ridge and a lower ridge for retaining the peristaltic tube.

4. The peristaltic pump as recited in claim 1, further comprising:
a second retaining shoe, the retaining shoe and the second retaining shoe coupled together.

5. The peristaltic pump as recited in claim 4, wherein the retaining shoe and the second retaining shoe are coupled together with a rod extending at least partially through the retaining shoe and the second retaining shoe.

6. The peristaltic pump as recited in claim 1, wherein the retaining shoe defines a receiver for receiving the keeper.

7. A system, comprising:
a rotating member configured to rotate about an axis;
a plurality of rollers coupled to the rotating member in a circular configuration, the plurality of rollers configured to orbit about the axis of the rotating member;
a peristaltic tube for receiving a fluid to be pumped;
a guide member defining a channel configured to guide a peristaltic tube configured to receive a fluid to be pumped around the rotating member so that the peristaltic tube is in proximity to the plurality of rollers;
a retaining shoe configured to pivot to press the peristaltic tube against the plurality of rollers, the retaining shoe comprising a plurality of surface irregularities, the plurality of surface irregularities configured to restrict movement of the peristaltic tube; and
a keeper configured to brace the retaining shoe against the peristaltic tube, wherein the keeper comprises an adjustment mechanism configured to brace the retaining shoe against the peristaltic tube by exerting a force on the retaining shoe opposite a pivot of the retaining shoe and in a direction generally toward the axis of the rotating member.

8. The system as recited in claim 7, wherein the rotating member comprises a top plate and a bottom plate for supporting the plurality of rollers.

9. The system as recited in claim 7, wherein the retaining shoe comprises an upper ridge and a lower ridge for retaining the peristaltic tube.

10. The system as recited in claim 7, further comprising:
a second retaining shoe, where the retaining shoe and the second retaining shoe are coupled together.

11. The system as recited in claim 10, wherein the retaining shoe and the second retaining shoe are coupled together with a rod extending at least partially through the retaining shoe and the second retaining shoe.

12. The system as recited in claim 7, wherein the retaining shoe defines a receiver for receiving the keeper.

13. A peristaltic pump, comprising:
a rotating member configured to rotate about an axis;
a plurality of rollers coupled to the rotating member in a circular configuration, the plurality of rollers configured to orbit about the axis of the rotating member;
a guide member coupled to the pump housing, the guide member defining a channel configured to guide a peristaltic tube around the rotating member so that the peristaltic tube is in proximity to the plurality of rollers;
a retaining shoe pivotally coupled to the pump housing, the retaining shoe configured to press the peristaltic tube against the plurality of rollers, the retaining shoe comprising a plurality of surface irregularities configured to restrict movement of the peristaltic tube, the retaining shoe comprising an upper ridge and a lower ridge for retaining the peristaltic tube; and
a keeper coupled to the pump housing, the keeper configured to brace the retaining shoe against the peristaltic tube, wherein the keeper comprises an adjustment mechanism configured to brace the retaining shoe against the peristaltic tube by exerting a force on the retaining shoe opposite a pivot of the retaining shoe and in a direction generally toward the axis of the rotating member.

14. The peristaltic pump as recited in claim 13, wherein the rotating member comprises a top plate and a bottom plate for supporting the plurality of rollers.

15. The peristaltic pump as recited in claim 13, further comprising:
a second retaining shoe, where the retaining shoe and the second retaining shoe are coupled together.

16. The peristaltic pump as recited in claim 15, wherein the retaining shoe and the second retaining shoe are coupled together with a rod extending at least partially through the retaining shoe and the second retaining shoe.

17. The peristaltic pump as recited in claim 13, wherein the retaining shoe defines a receiver for receiving the keeper.

\* \* \* \* \*